United States Patent
Goris et al.

(10) Patent No.: US 9,776,937 B2
(45) Date of Patent: Oct. 3, 2017

(54) INTEGRATED NITRILE POISON ADSORPTION AND DESORPTION SYSTEM

(75) Inventors: Hans K. T. Goris, Laakdal (BE); Geraldine Tosin, Notre Dame de Gaavenchon (FR); Luc R. M. Martens, Meise (BE); Machteld M. Mertens, Flemington, NJ (US); Silvio Carrettin, Kraainem (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 512 days.

(21) Appl. No.: 14/233,192

(22) PCT Filed: Jun. 14, 2012

(86) PCT No.: PCT/EP2012/061365
§ 371 (c)(1),
(2), (4) Date: Mar. 26, 2014

(87) PCT Pub. No.: WO2013/013885
PCT Pub. Date: Jan. 31, 2013

(65) Prior Publication Data
US 2014/0330060 A1 Nov. 6, 2014

(30) Foreign Application Priority Data

Jul. 25, 2011 (EP) .................... 11175234

(51) Int. Cl.
*C07C 7/12* (2006.01)
*C07C 7/10* (2006.01)
*C07C 2/12* (2006.01)
*C07C 2/10* (2006.01)
(Continued)

(52) U.S. Cl.
CPC .................. *C07C 7/12* (2013.01); *B01J 20/06* (2013.01); *B01J 20/08* (2013.01); *B01J 20/12* (2013.01);
(Continued)

(58) Field of Classification Search
CPC ..... C07C 7/12; C07C 2/12; C07C 2/10; C07C 2/18
See application file for complete search history.

(56) References Cited

U.S. PATENT DOCUMENTS

| | | |
|---|---|---|
| 3,922,217 A | 11/1975 | Cohen et al. |
| 4,973,790 A | 11/1990 | Beech, Jr. et al. |
| (Continued) | | |

FOREIGN PATENT DOCUMENTS

| | | |
|---|---|---|
| EP | 1 216 978 | 6/2002 |
| WO | WO 02/060842 | 8/2002 |

OTHER PUBLICATIONS

Ramirez-Corrodores et al., "Options for Nitriles Removal from $C_4$-$C_5$ Cuts: 1. Via Adsorption," Adsorption Science & Technology, vol. 23, No. 10, 2005, pp. 813-825.

Stepanov et al., "Interaciton of Acetonitrile with Olefins and Alcohols in Zeolite H-ZSM-5: In Situ Solid-State NMR Characterization of the Reaction Products," Chem. Eur. J. 1997, 3, No. 1, pp. 47-56.

*Primary Examiner* — In Suk Bullock
*Assistant Examiner* — Youngsul Jeong
(74) *Attorney, Agent, or Firm* — Darryl M. Tyus

(57) ABSTRACT

In a feed clean-up process at least two adsorbents (2, 4) are installed in front of an oligomerization reactor (3). Olefin feed is sent over one adsorbent (2) and the nitrile poisons are adsorbed so that clean feed will enter the reactor (3). Before the adsorbent (2) will be saturated, the feed (1) is sent to the other, fresh adsorbent (4). At the same time oligomerization product from the reactor (3) is used to desorb nitriles from the spent adsorbent (2).

14 Claims, 1 Drawing Sheet

(51) Int. Cl.
  *C07C 2/18*      (2006.01)
  *C07C 7/13*      (2006.01)
  *B01J 20/06*     (2006.01)
  *B01J 20/08*     (2006.01)
  *B01J 20/12*     (2006.01)
  *B01J 20/18*     (2006.01)
  *B01J 20/20*     (2006.01)
  *B01J 20/34*     (2006.01)

(52) U.S. Cl.
  CPC ............. *B01J 20/18* (2013.01); *B01J 20/186* (2013.01); *B01J 20/20* (2013.01); *B01J 20/3408* (2013.01); *B01J 20/3483* (2013.01); *C07C 2/10* (2013.01); *C07C 2/12* (2013.01); *C07C 2/18* (2013.01); *C07C 7/13* (2013.01); *B01J 2220/606* (2013.01); *C07C 2523/755* (2013.01); *C07C 2527/173* (2013.01)

(56) References Cited

U.S. PATENT DOCUMENTS

| | | | |
|---|---|---|---|
| 5,414,183 | A | 5/1995 | Abrevaya et al. |
| 5,744,686 | A | 4/1998 | Gajda |
| 6,019,887 | A * | 2/2000 | Ramirez de Agudelo ................ B01D 15/00 208/254 R |
| 2002/0111523 | A1 | 8/2002 | Mathys et al. |
| 2002/0112992 | A1* | 8/2002 | Johnson .................... C07C 7/12 208/305 |
| 2005/0137442 | A1 | 6/2005 | Gajda et al. |
| 2007/0086933 | A1 | 4/2007 | Negiz et al. |
| 2008/0194903 | A1 | 8/2008 | Schubert et al. |
| 2008/0312484 | A1* | 12/2008 | Godsmark ................ C07C 2/12 585/520 |

\* cited by examiner

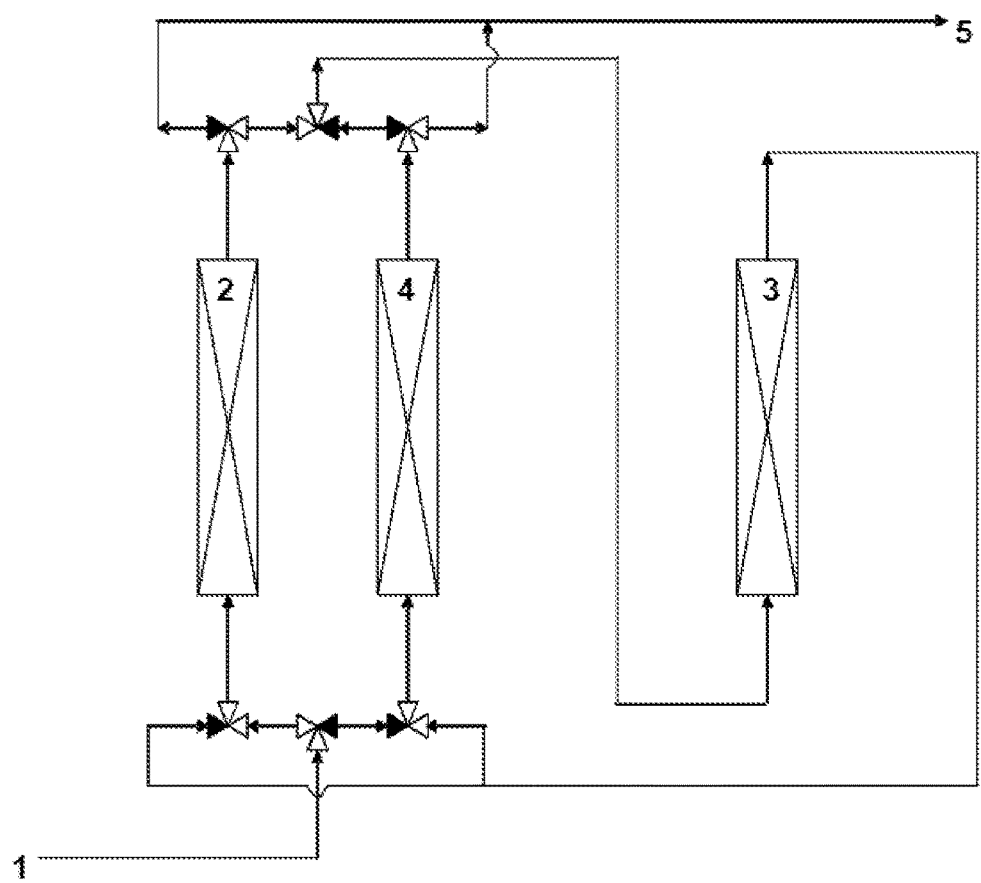

INTEGRATED NITRILE POISON ADSORPTION AND DESORPTION SYSTEM

CROSS REFERENCE TO RELATED APPLICATIONS

This application is a National Stage Application of International Application No. PCT/EP2010/061365, filed Jun. 14, 2012, the disclosure of which is incorporated by reference in its entirety.

FIELD OF THE INVENTION

The present invention relates to a process for removing nitriles from hydrocarbon feeds.

BACKGROUND OF THE INVENTION

The higher olefins oligomerization process converts light olefins, typically, $C_3$ to $C_6$ light olefins, to oligomers (higher olefins), typically such as octenes, nonenes and dodecenes. These higher olefins are then used in the production of various products such as plasticizers and solvents. The feedstocks used for the higher olefins oligomerization process come from various sources, such as catalytic crackers and steam crackers. Such feeds are known to contain nitrogen containing compounds, which act as poisons for the catalysts typically used in the higher olefins oligomerization process. The presence of poisons in the feeds has a significant impact on the catalyst life, and thus on the operation and economics of the higher olefins oligomerization process. It is known that acidic catalysts like solid phosphoric acid or zeolites typically used in olefin oligomerization processes are susceptible to poisoning from trace amounts of sulphur-, nitrogen- and oxygen-containing compounds in the feed. Such poisons adsorb on the acidic catalysts, blocking acid sites and pores. This causes enhanced deactivation of the catalyst and shorter catalyst life. Special precautions and feed cleanup is required in case the poison levels are too high.

At present there is no known single process that can quantitatively remove all nitrogen poisons from olefin feeds useful in the higher olefins oligomerization process to meet required feed quality specifications. Water washing only partially removes nitriles, such as acetonitrile, from certain olefin feeds. Not only is the removal process difficult but it is expensive and generates a lot of waste water.

It is known that commercial guard beds such as Selexsorb CD alumina guard bed can adsorb nitriles from propene, butene and/or pentene-containing feedstreams. Unfortunately, the guard bed capacity is too low to achieve the commercial run lengths, particularly when these commercial feeds contain 5 to 80 ppm acetonitrile and/or propionitrile. A common practice is to regenerate spent guard bed by heating under e.g. a nitrogen flow, or a hydrocarbon flow which is free of nitriles to achieve full desorption form the guard bed. For example EP1216978 mentions isopentane as the desorbing solvent. Adsorption Science & Technology Vol. 23 No. 10 2005 p. 813 to 825 "Options for Nitriles Removal from $C_4$-$C_5$ Cuts: 1. Via Adsorption" by M. M Ramirez-Corrodores et al. discloses use of methanol or pentane as a desorbent. However, such processes require an extra supply of nitrogen or hydrocarbons as well as the corresponding additional apparatus features. This is therefore costly and also proves to be a discontinuous process requiring regular replacement of the nitrogen and hydrocarbon desorbents. Such processes also have the disadvantage of generating waste streams that require special handling.

The interaction of acetonitrile with olefins and alcohols in zeolite H-ZSM-5 is described in Chem. Eur. J. 1997, 3, No. 1 pages 47 to 56 "Interaction of Acetonitrile with Olefins and Alcohols in Zeolite H-ZSM-5: In-Situ Solid-State NMR Characterization of the Reaction Products" Alexander G. Stepanov and Mikhail v. Luzgin.

U.S. Pat. No. 5,414,183 discloses isomerization and etherification reactions. Nitrogen contaminants in the hydrocarbon feed stream are converted to hydrolysis products by contact with an alkaline solution. Residual products in the hydrocarbon phase may be removed by a variety of known means including water washing, stripping and adsorption. Spent adsorbent is regenerated in the vapour phase using a contaminant free stream including one or more of hydrogen, nitrogen fuel gas, natural gas, and clean light hydrocarbons such as propane, butanes, and/or pentanes.

U.S. Pat. No. 4,973,790 discloses a process for oligomerizing $C_2$ to $C_{10}$ olefins obtained by catalytic cracking of heavy crude oil. Feed pretreatment is practised to remove basic nitrogen compounds present in the light olefin feed with a water wash or guard bed. Ion exchange resins which are used to take out basic nitrogen from the feed only work one time and cannot be regenerated. Zeolitic guard beds may be regenerated by heating. Oxidative regeneration is used for alumina.

US 2005/0137442 relates to a transalkylation process where organic nitrogen compounds, including acetonitrile and propionitrile, are removed from an aromatic feed stream by contacting the stream with an acidic molecular sieve at a temperature of at least 120° C. The adsorption bed may be regenerated with a hot natural gas stream or by a carbon burn.

U.S. Pat. No. 5,744,686 discloses a process for removal of nitrogen compounds from an aromatic hydrocarbon stream. The process includes a fractionation zone and an adsorption zone where the feedstream is passed to the fractionation zone to provide a dry bottoms product stream essentially free of the nitrogen compounds and an overhead stream. The overhead stream is condensed to provide an aqueous stream and a hydrocarbon stream. The hydrocarbon stream is passed to an adsorption zone and a treated effluent recovered therefrom is returned to the fractionation zone.

US2007/0086933 discloses a transalkylation process for reacting carbon number nine aromatics with toluene to form carbon number eight aromatics such a para-xylene. The process uses an alumina guard bed in order to remove chlorides from the aromatic feed prior to contacting with a transalkylation catalyst. The transalkylation effluent is recycled partially to the transalkylation zone or the alumina guard bed zone.

SUMMARY OF THE INVENTION

The present invention provides a continuous process for converting a hydrocarbon feed contaminated with nitrile into a hydrocarbon product, the process comprising the steps of:
i) in a first adsorber, contacting a hydrocarbon feed comprising nitriles with at least one adsorbent in order to remove nitriles from the feed;
ii) converting the feed with reduced level of nitriles into a hydrocarbon product; iii) switching the flow of hydrocarbon feed comprising nitriles from the first adsorber to a second adsorber, and contacting the hydrocarbon feed comprising nitriles with at least one adsorbent in said second adsorber in order to remove nitriles from the feed; and iv) while step iii) is taking place, desorbing the nitriles adsorbed on the at least one adsorbent of the first adsorber with a portion of the hydrocarbon product obtained in step ii). Preferably the switching is automated.

In one embodiment the first adsorber and the second adsorber are equipped with tube heating.

Additionally or alternatively, the first and second adsorbers are heated by the heat generated during step (ii).

Preferably nitrile adsorption in step i) is carried out at a temperature of 20° C. to 60° C. and nitrile desorption in step iv) is carried out at a temperature of 150° C. to 250° C.

The nitrile may be selected from acetonitrile, propionitrile and mixtures thereof.

Preferably the hydrocarbon feed and the hydrocarbon product acting as the desorption stream flow counter-currently.

In an embodiment the hydrocarbon feed comprises an olefin and the conditions in step ii) are suitable to oligomerize the olefin. Preferably the olefin is selected from olefins having 3 to 6 carbon atoms, preferably from 3 to 5 carbon atoms.

The present invention further provides the use of a hydrocarbon product made from a hydrocarbon feed comprising olefins having from 2 to 6 carbon atoms to desorb nitriles from an adsorbent, which adsorbent comprises nitriles adsorbed from the hydrocarbon feed. Preferably the hydrocarbon product is an olefin oligomer or an alkyl benzene.

One of the unique aspects of the present invention is to use the hydrocarbon product stream generated from the hydrocarbon feed stream as the desorbing solvent. It is known that adsorbed species can be desorbed with pure hydrocarbons. However, the present invention describes how the product stream from a reaction is used and sent back to the spent adsorbent, so that nitriles can desorb and end up in the product stream.

Whilst the background of the present invention has been described in the context of the higher olefins reaction, the solution of the present invention for nitrile removal can also be applied to any other process and for any other hydrocarbon feed where nitriles form a poison problem, for example in aromatics production, olefin isomerizations and alkylations.

BRIEF DESCRIPTION OF THE DRAWINGS

The FIGURE represents a scheme for an embodiment according to the present invention.

DETAILED DESCRIPTION

Hydrocarbon Feed

The hydrocarbon feed according to the present invention can be any hydrocarbon feed contaminated with nitriles, including aromatic or aliphatic hydrocarbons or a combination thereof. Whilst the process of the present invention is not limited by hydrocarbon feed or the type of process for which the hydrocarbon feed is used, preferably the process of the present invention is part of an olefin oligomerization process and the hydrocarbon feed is an olefin feed.

As used herein, "olefins" refers to any unsaturated hydrocarbons having the formula $C_nH_{2n}$, wherein C is a carbon atom, H is a hydrogen atom, and n is the number of carbon atoms in the olefin. According to this invention, the olefins in the feed typically have from 2 to 15 carbon atoms, such as at least 3 and no more than 8 carbon atoms, and typically at least 3 and no more than 6 carbon atoms. They are also referred to as lower olefins. The feed may also comprise one or more paraffins. As used herein, "paraffins" refers to any of the saturated hydrocarbons having the formula $C_nH_{2n+2}$, wherein C is a carbon atom, H is a hydrogen atom, and n is the number of carbon atoms in the paraffin. The paraffins that may be present in the olefin feed typically have from 1 to 25 carbon atoms, such as from 1 to 15 carbon atoms, and conveniently at least 3 and no more than 6 carbon atoms. Examples of suitable paraffins include methane, ethane, propane, butane, pentane, hexane, isomers thereof and mixtures thereof. If present in the feed, the paraffins may have the same or a different number of carbon atoms as the olefins.

If present, the paraffin acts as a diluent. If used, the olefin feed may comprise at least 10%, at least 25%, at least 30%, at least 35%, or at least 40% paraffin, based upon the total volume of the feed. Alternatively stated, if used, the diluent may be present in the olefin feed in the range from 10% to 40%, alternatively, from 10% to 35%, and alternatively, from 20% to 35% based upon the total volume of the feed. The diluent may also be fed to the reactor(s) separately from the olefin feed. When fed separately, the diluent may be fed in amounts equivalent to those mentioned above, where the diluent is co-fed with the feed. These amounts may not necessarily be the same as the ranges stated above given that more or less of the diluent may be necessary when fed separately to provide an equivalent.

In a class of embodiments, the olefin feed comprises olefins selected from propene, butenes, pentenes, hexenes, their isomers, and mixtures thereof. The process of this invention is especially useful for the oligomerization of feeds comprising propene, butenes, pentenes, their isomers, and mixtures thereof. As used herein, "isomers" refers to compounds having the same molecular formula but different structural formula.

Additionally, the feed may comprise an oligomer (higher olefin), for example, a dimer, such as one provided by recycling a part of an olefin oligomerization product stream. As used herein, "oligomer(s)" or "oligomer product" refers to an olefin (or a mixture of olefins) made from a few light olefins. For example, oligomers include dimers, trimers, tetramers, obtained from two, three or four light olefins of the same number of carbon atoms, mixed oligomers, obtained from 2 or more olefins having different numbers of carbon atoms and mixtures thereof. In a class of embodiments, "oligomer(s)" refers to an olefin (or a mixture of olefins) having 20 carbon atoms or less, alternatively, 15 carbon atoms or less, such as 10 carbon atoms or less, alternatively, 9 carbon atoms or less, and conveniently, 8 carbon atoms or less, that has been obtained by linking two or more light olefins together. As used herein, "oligomerization process" refers to any process by which light olefins are linked together to form the oligomer(s) as defined above. As used herein, the term "oligomerization conditions" refers to any and all those variations of equipment, conditions (e.g. temperatures, pressures, weight hourly space velocities etc.), materials, and reactor schemes that are suitable to conduct the oligomerization process to produce the oligomer(s) as known and applied in the art and discussed more below.

In a class of embodiments, the feed comprises 30 wt % or more olefins, such as 40 wt % or more olefins, alternatively, 50 wt % or more olefins, alternatively, 60 wt % or more olefins, alternatively, 70 wt % or more olefins, and alternatively, 80 wt % or more olefins, based upon the total weight of the olefin feed.

In any of the olefin oligomerization embodiments described herein, the feed should be totally free, or at least substantially free, of aromatic hydrocarbon compounds that consist solely of hydrogen and carbon atoms. In this context, "substantially free" means that the olefin feed contains 25 wt % or less, preferably 15 wt % or less, more preferably 10 wt % or less, such as 5 wt % or less, and most preferably 1 wt % or less aromatic hydrocarbon, based upon the total weight of the olefin feed.

Examples of suitable olefin feeds include untreated refinery streams such as Fluidized Catalytic Cracking (FCC) streams, coker streams, pyrolysis gasoline streams or reformates.

Other examples of suitable olefin feeds include refinery feeds often referred to as Raffinate-1 (RAF-1), Raffinate-2 (RAF-2) or Raffinate-3 (RAF-3). Typically, Raffinate-1, Raffinate-2 and Raffinate-3 may be regarded as streams obtainable at various stages in the processing of crude $C_4$ streams obtained from petroleum refining processes. These streams are usually from olefin steam crackers but may also come from refinery catalytic crackers, in which case they generally contain the same components but in different proportions. The first stage of processing these crude $C_4$ refinery streams is to remove butadiene from these streams, such as by solvent extraction or hydrogenation. Butadiene is generally present in the crude $C_4$ refinery streams as 40-45 wt. % of the stream. The product obtained after butadiene removal is Raffinate-1. It generally consists of isobutylene, the two isomers of n-butane, 1-butene and 2-butene, and smaller quantities of butanes and other compounds. The next step consists in removing isobutylene, usually by reaction of isobutylene with methanol to produce methyl-tert-butylether (MTBE), which then produces Raffinate-2. Raffinate-3 (RAF-3) is less common but may be obtained after separation of 1-butene from Raffinate 2. Raffinate-3 typically has a residual 1-butene content of about 1%.

In another embodiment, the feed comprises an FCC light olefin stream that typically comprises ethane, ethylene, propane, propylene, isobutane, n-butane, butenes, pentanes, and other optional components.

According to the present invention, any of the above-described feeds contains organic nitrile contaminants which must be removed to an acceptable level before the hydrocarbon feed undergoes reaction. As used herein, "nitrile" is any organic compound that has a nitrile group (or —C≡N functional group). In the nitrile group, the carbon atom and the nitrogen atom are triple bonded together. As used herein, "acetonitrile" (ACN) is the chemical compound with formula $CH_3CN$. This colorless liquid is the simplest organic nitrile. As used herein, "propanenitrile", "propionitrile", or "ethyl cyanide" is a nitrile with the molecular formula $C_2H_5CN$ and the terms may be used interchangeably. It is also a clear liquid. As used herein, "nitrile" may also refer to heavier nitriles. Preferably the nitrile removed is a C3 to C5 nitrile. In the most preferred embodiment the nitrile to be removed is any of acetonitrile and propionitrile. These compounds are especially toxic to oligomerization catalysts and their removal leads to significant catalyst life improvement.

Typically, the nitrile content in the hydrocarbon feed upstream of the adsorbent may be about 3 ppm or more, such as about 5 ppm or more, typically, 10 ppm or more, such as 20 ppm or more, and yet alternatively, 30 ppm or more, calculated on a nitrogen atom basis by weight (wt ppm), with respect to the total weight of hydrocarbon in the stream.

Adsorbents and Nitrile Removal Process

The present invention describes a continuous process in which at least two adsorbers, hereinafter referred to as the first adsorber and the second adsorber, respectively, are installed in front of a reactor for a desired reaction. Both the first and second adsorber contain at least one adsorbent. The hydrocarbon feed is sent to the first adsorber, where the nitrile contaminants present in the hydrocarbon feed are adsorbed, so that clean feed, i.e. a feed with reduced nitrile content, will enter the reactor in which conversion of the hydrocarbon feed to a hydrocarbon product will take place. Over time, the adsorbent present in the first adsorber will adsorb more and more nitriles. Before the adsorbent is saturated with nitriles and becomes ineffective, the hydrocarbon feed is sent to a second adsorber, containing fresh adsorbent. While the hydrocarbon feed is fed through the second adsorber, and production of the desired hydrocarbon product continues, the nitriles that have adsorbed on the adsorbent in the first adsorber are desorbed. A portion of the hydrocarbon product is used for this purpose. By "portion" it is meant at least part of the hydrocarbon product. Therefore portion may refer to a part or all of the hydrocarbon product. Examples of hydrocarbon product include all or a fraction of propene, butene and pentene oligomerization products such as hexenes, heptenes, octenes, nonenes, decenes, undecenes, dodecenes, tetramers and tridecenes.

Additionally or alternatively, a direct derivative of the hydrocarbon product can be used as the desorption agent. Examples of derivatives include the hydrogenated oligomerization products such as hexanes, heptanes, octanes, nonanes, decanes, undecanes, dodecanes and tridecanes.

Preferably the hydrocarbon feed and the hydrocarbon product flow countercurrently to avoid mixing of the streams.

The adsorbents of used in the first and second adsorber can be made of the same or different material. Examples of suitable adsorbents include alumina (aluminium oxide), preferably gamma alumina or eta alumina, zeolites (acidic or cation-exchanged), activated carbons, clays, metal oxides and mixed metal oxides. Examples of metal oxides other than alumina include tin oxide, zirconium oxide, titanium oxide, iron oxide, magnesium and tungsten oxide, silicon oxide, copper oxide, nickel oxide, zinc oxide, and mixtures thereof. The adsorbent can comprise two or more of the metal oxides listed above and in any combination. There are different ways to prepare multi metal oxide compositions, including physical mixing and co-precipitation methods. The metal oxide or multi metal oxide used as the adsorbent may also contain metals and noble metals added to the metal oxide or multi metal oxide by impregnation or other preparation methods.

Preferably the adsorbent may comprise a zeolite with faujasite structure. The preferred zeolites with faujasite structure comprise Zeolite X or Zeolite Y. Preferred adsorbents include sodium Zeolite Y (NaY) and sodium Zeolite X (NaX).

Whilst the switching of the feed stream between the first and second adsorber can be controlled by several means, including manual control, it is preferred that the switching is valve-controlled. This ensures the possibility of timing and automating the switching. Valves can be installed which direct the flows to the appropriate adsorber. The switching can then be done before harmful quantities of nitriles are detected in the feed stream at the exit of the adsorbers. The switching frequency will depend on several parameters such as nitrile concentration in the feed, guard bed capacity and weight hourly space velocity (WHSV).

The adsorption may be carried out a room temperature or elevated temperatures, and thus conveniently takes place in the range of 20 to 200° C. Desorption is preferably carried out at an elevated temperature, conveniently in the range of 100 to 400° C. Preferably, adsorption is carried out in the temperature range of 20 to 60° C. and desorption is carried out in the temperature range of 150 to 250° C. to achieve optimal rates of nitrile adsorption and desorption.

While adsorption and desorption can be carried out at room temperature, it is preferred that tube heating is provided in the adsorber, to allow efficient desorption at elevated temperatures. Alternatively, heat generated by the desired reaction in the production of the hydrocarbon stream can be used to achieve elevated temperatures. In this way, no extra heating apparatus is required and energy is saved. Additionally, both tube heating and heat generated from the production of the hydrocarbon stream can be used to heat the adsorbers, so that if tube heating fails, the heat generated from the desired hydrocarbon feed conversion can still ensure nitrile desorption at an optimal temperature.

The pressure employed during adsorption may be in the range of from about 400 psig to about 4000 psig (2860 kPa to 27688 kPa), and preferably from about 500 psig to about 1500 psig (3550 kPa to 10446 kPa). The hydrocarbon feed weight hourly space velocity may be in the range of from about 0.1 hr-1 to about 20 hr-1, and preferably from about 0.5 hr$^{-1}$ to about 5 hr$^{-1}$.

The process can also comprise more than two adsorbers for alternative feed switching options and to achieve even longer run lengths. As soon as nitrile desorption is complete, the flow of hydrocarbon product going through the first adsorber is stopped, and the first adsorber is ready to be used again to adsorb nitriles from the feed. The hydrocarbon product containing desorbed nitrile is combined with other desired hydrocarbon product, since nitrile contamination is typically no longer a problem downstream of the hydrocarbon feed conversion reactor.

After contact with the adsorbent in first or second adsorber, the nitrile content in the hydrocarbon stream downstream of the adsorbers is about 1.50 ppm or less, alternatively, 1.00 ppm or less, such as 0.50 ppm or less, alternatively, 0.30 ppm or less, 0.20 ppm or less, and yet preferably 0.10 ppm or less calculated on a nitrogen atomic basis by weight (wt ppm) relative to the total weight of hydrocarbons in the olefin stream.

Overall advantages of the nitrile removal process of the present invention include: no waste streams are generated, since the product of feed conversion is used, no dedicated desorbing solvent is consumed and no water wash is required to extract the nitriles from the hydrocarbon stream. Furthermore, no additional desorbing solvent handling such as storage, transfer and cleanup is required. The hydrocarbon product stream, having a higher density than desorption solvents used up to now, is more effective than lower density solvents. By switching the flow between the first and second adsorbers, and simultaneous nitrile desorption with the hydrocarbon product stream for adsorbent regeneration, a continuous process is established.

Formation of the Hydrocarbon Product

The catalyst used in step ii) the process of the present invention depends on the desired reaction and product to be obtained. While the process of the invention will be illustrated in more detail in the context of a continuous olefin oligomerization process, the principles of contaminant adsorption and desorption disclosed herein could easily be used for other hydrocarbon conversion processes.

In the context of an olefin oligomerization process, feed conversion to a hydrocarbon product preferably takes place by contacting an olefin feed with reduced nitrile content with an olefin oligomerization catalyst. Further conversion of the hydrocarbon product to a derivative of the product can also be carried out.

One or more catalysts may be used for the oligomerization. Any catalyst suitable for olefin oligomerization, whether homogeneous or heterogeneous, may be used, Heterogeneous catalysts may be crystalline or amorphous (non-crystalline) catalysts. Crystalline catalysts include without limitation molecular sieve catalysts such as, for example, zeolite catalysts, in particular, H-zeolites (i.e. zeolites in their proton or acidic form).

Non-crystalline heterogeneous catalysts include without limitation solid acid catalysts such as, for example, solid phosphoric acid (SPA) catalysts and supported metal catalysts or supported metal oxide catalysts. Non-limiting examples of olefin oligomerization processes using such catalysts may be found as follows: Olefin oligomerization using SPA catalysts is disclosed for example in U.S. Pat. No. 6,025,533, WO 92/13818 or WO 2005/058777. The CAT-POLY™ Process (UOP and Sud Chemie) employs phosphoric acid on a silica support. The OCTOL™ Process (UOP/Huels (now Evonik)) employs a nickel containing catalyst on a silica/aluminium oxide support. See Make plasticizer olefins via n-butene dimerization R. H, Friedlander et al., Hydrocarbon Processing, February 1986, pages 31-33, and U.S. Pat. No. 5,177,282. Amorphous silica aluminium oxide supports are useful and commonly utilized. Solid acid catalysts may be optionally practiced with promoters such as TaF5.

In another embodiment, olefin oligomerization can take place in the presence of a homogenous catalyst. Non-limiting examples of such catalysts are provided as follows. The IFP (now Axens) DIMERSOL® processes employ a Ni-based homogeneous catalyst. (Y. Chauvin et al. Chemistry and Industry, 1974, 373-378). U.S. Pat. No. 4,225,743 discloses a homogeneous catalyst system suitable for olefin oligomerization, consisting of a Nickel (II) salt of octanoic acid, ethylaluminium dichloride, and a free fatty acid. Preferably, the catalyst is selected from catalysts comprising a zeolite, nickel oxide or phosphoric acid.

The term "zeolites" is often used to describe the aluminosilicate members of the family of microporous solids known as "molecular sieves". The term molecular sieve refers to a particular property of these materials, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon or aluminum atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites may not be cylindrical.

In an embodiment, the at least one zeolite catalyst may include a medium pore size molecular sieve having a Constraint Index of about 1 to about 12. Constraint Index and a method of its determination are described in, for example, U.S. Pat. No. 4,016,218.

Examples of the at least one zeolite catalyst include those of the TON framework type (for example, ZSM-22, ISI-1, Theta-1, Nu-10, and KZ-2), those of the MTT framework type (for example, ZSM-23 and KZ-1), those of the MFI framework type (for example, ZSM-5), those of the MFS framework type (for example, ZSM-57), those of the MEL framework type (for example, ZSM-11), those of the MTW framework type (for example, ZSM-12), those of the EUO framework type (for example, EU-1), those of the AEL framework type (for example, SAPO-11), members of the ferrierite family (for example, ZSM-35) and members of the ZSM-48 family of molecular sieves (for example, ZSM-48). Other examples include zeolites of the MWW family (e.g., MCM-22, MCM-48), zeolites of the MOR framework type, or zeolite beta. As used herein, the term "structure type" is used as described in the Structure Type Atlas, Zeolites 17, 1996.

Preferably, the zeolite is selected from at least one of zeolites having the TON framework type, for example ZSM-22, ZSM-5, ZSM-11, ZSM-12, ZSM-18, ZSM-22, ZSM-23, ZSM-35, ZSM-38, ZSM-48, ZSM-50, zeolites of the MFS framework type, for example ZSM-57, and mixtures thereof.

Mixtures of two or more of zeolites may be used in the oligomerization process. For example, the mixture may include ZSM-22 and ZSM-57 or ZSM-22 and ZSM-5 or ZSM-57 and ZSM-5. The at least one zeolite catalyst may also be combined with other types of catalysts such as a solid phosphoric acid (sPa) catalyst.

The zeolite used in the oligomerization catalyst may have an average crystallite or particle size of up to 15 µm, such as within the range of from 0.01 to 6 µm, alternatively, from 0.05 to 5 µm, and alternatively, from 0.1 to 3 µm. As used herein, "average particle size" refers to the arithmetic average of the diameter distribution of the crystals on a volume basis.

Preferably, the zeolite is used in its proton, or acidic form. To obtain this form, an as-synthesized molecular sieve that has been obtained in an alkaline or alkaline-metal form is advantageously converted to its acid form, for example, by acid treatment, e.g., by $HC_1$, acetic acid, etc. or by ion exchange, for example, ammonium ion exchange. Subsequently, it may undergo calcination before use. The calcined materials may be post-treated, such as by steaming.

The at least one zeolite catalyst may be produced by any suitable method known for the given type of zeolite. One technique includes heating a reaction mixture containing a source of silicon oxide, a source of aluminum oxide and, if appropriate, an organic promoter, for example, a nitrogen or phosphorus-containing organic base, together optionally, with an alkali metal base, and separating the porous aluminosilicate crystals (zeolite precursor crystals) formed. The precursor crystals are then calcined in air or oxygen at a temperature exceeding or about 500° C., for example, at a temperature of 550° C. for about 10 to about 20 hours. As recognized in the art, calcination temperatures and durations may vary depending on the type of zeolite catalyst or combination of zeolite catalysts selected. In one embodiment, the calcined material is exchanged with ammonium ions ($NH_{4+}$) and subjected to conditions under which the ammonium ions decompose, with the formation of ammonia and a proton, thus, producing an acidic form of the at least one zeolite catalyst. Alternatively, the acidic form of the catalyst may be obtained by acid exchange with hydrochloric acid, acetic acid, etc. If desired, however, the calcined material may be used as a catalyst without first being exchanged with ammonium ions, since the material already possesses acidic sites.

Ammonium exchanged and calcined monodimensional 10-rings zeolites (e.g., ZSM-22 and ZSM-23) may be treated to selectivate their surface, thereby, forming a selectivated catalyst. This selectivation may be achieved in numerous ways. In an embodiment, the at least one zeolite catalyst may be titrated with an organic nitrogen base, such as collidine. See, for example, U.S. Pat. No. 5,026,933. Another example is by depositing a crystalline Si:Al layer on a core of zeolite where this layer has a higher Si:Al ratio than the untreated zeolite. See, for example, U.S. Pat. No. 6,013,851.

Although much of the discussion above is directed to aluminosilicate zeolites, it is possible to use material in which silicon and aluminum have been replaced in whole or in part by other elements, for example, any one or more of a Group 2 to Group 15 atom. For example, silicon may be replaced by or contacted with germanium and aluminum or may be replaced with boron, gallium, chromium, and iron. As used herein, these materials containing such replacement lattice elements may also be termed zeolites.

It may be desirable to incorporate the molecular sieves or zeolites mentioned above with another material that is resistant to the temperatures and other conditions employed in the olefin oligomerization process. Thus the molecular sieves or zeolites may be used in the form of an extrudate with binder, where the molecular sieve or zeolite is dispersed within a conventional binder. Binding is typically done by forming a pill, sphere, or extrudate. The extrudate is usually formed by extruding the molecular sieve, optionally in the presence of a binder, and drying and calcining the resulting extrudate. The binder materials used are resistant to the temperatures and other conditions, e.g., mechanical attrition, which occur in various hydrocarbon conversion processes.

Examples of binder materials that may be employed with the molecular sieves or zeolites suitable for use in the process of the invention include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. Examples of other materials include porous matrix materials such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Advantageously, a binder free version of the zeolite may be used.

Exemplary catalyst materials and processes for making such catalysts may also be found in U.S. Pat. Nos. 3,960,978, 4,016,218, 4,021,502, 4,381,255, 4,560,536, 4,919,896, 5,446,222, 5,672,800, 6,143,942, 6,517,807, 6,884,914, U.S. Patent Application Publication No. 2006/0199987, EP 746 538 A, WO 1994/12452 WO 2005/118512, WO 2005/118513, WO 2007/006398, and WO 2008/088452. See also "Atlas of Zeolite Structure Types," Eds. W. H. Meier, D. H. Olson and Ch. Baerlocher, Elsevier, Fourth Edition, 1996.

According to the present invention, the olefin feed with reduced level of nitriles is contacted with a catalyst under conditions suitable to oligomerize the olefins. The olefin oligomerization reaction system may include one or more of a fixed bed reactor, a packed bed reactor, a tubular reactor, a fluidized bed reactor, a slurry reactor, a continuous catalyst regeneration reactor, and any combination thereof. These reactors may be operated in any combination such as, for example, in series and/or parallel sequence. In several embodiments, they may be operated in semi-continuous (i.e., continuous but down for routine maintenance), continuous, or batch mode.

The oligomerization conditions may temperatures from about 80° C. to about 350° C. Close to and above the upper end of the range, deoligomerization rates increase and may predominate over the oligomerization reaction providing an upper limit to practical operation. More typically, the reaction temperature is from about 130° C. to about 320° C., preferably from about 135° C. to about 310° C., and even more preferably from about 160° C. to about 270° C.

The pressure may be in the range of from about 400 psig to about 4000 psig (2860 to 27688 kPa), and alternatively, from about 500 psig to about 1500 psig (3550 to 10446 kPa). The olefin weight hourly space velocity based on catalyst, may be in the range of from about $0.1\ hr^{-1}$ to about $20\ hr^{-1}$ or from about $0.5\ hr^{-1}$ to about $5\ hr^{-1}$.

In one embodiment, process is conducted at a temperature of 80-350° C.; an olefin weight hourly space velocity of $0.1\text{-}20\ hr^{-1}$; and a pressure of 2860-27688 kPa.

In another embodiment, the process is conducted at a temperature of 130-320° C.; an olefin weight hourly space velocity of $0.5\text{-}5\ hr^{-1}$; and a pressure of 3550-10446 kPa.

Optionally, the olefin feed may also be hydrated (i.e., contacted with water) prior to oligomerization. In an embodiment, sufficient water is used to saturate the feed. In particular, the feed may comprise from about 0.01 to about 0.25, alternatively, from about 0.02 to about 0.20, and alternatively, from about 0.03 to about 0.10, mol % water based on the total hydrocarbon content of the feed. If desired and by way of example, the water content of the feed may be increased by passage through a thermostatted water saturator. The olefin feed used in the oligomerization step can therefore be wet or dry.

In a class of embodiments, the oligomers formed in the olefin oligomerization step of the process of the invention may include a hydrocarbon composition comprising at least 80 wt %, alternatively, at least 90 wt % based upon the total weight of the reactor effluent (the final reactor effluent if one or more reactors are utilized) of $C_6$ to $C_{20+}$ olefin or a mixture thereof.

The oligomer (higher olefin) product is useful in many applications and is the starting material for further conversion processes. For example, the oligomer product may be polymerized to produce polyolefins that have application in the plastic industry or polymerized to form synthetic basestocks for lubricants. The oligomer product may undergo hydroformylation and subsequently hydrogenation to produce alcohols. The alcohols may be used in industry such as, for example, solvents, or be incorporated into the production of detergents/surfactants. The alcohols may further be used in many other areas of industry such as, for example, undergoing esterification to produce esters that have application as plasticizers. The oligomer product may also be a blend component for fuels.

The present invention will be further described by reference to the FIGURE, which illustrates an embodiment according to the present invention.

A hydrocarbon feed (1) comprising pentene contaminated with propionitrile enters the first adsorber (2) where acetonitrile is adsorbed from the feed on a bed of gamma alumina at ambient temperature. After the first adsorber (2), the feed with reduced level of propionitrile is fed to an oligomerization reactor (3) containing ZSM 22 and ZSM 57 zeolite catalysts. Before compete saturation of gamma alumina with nitriles in the first adsorber, the hydrocarbon feed (1) is switched to a second adsorber (4), also containing gamma alumina. While the hydrocarbon feed is fed through adsorber (4), a portion of oligomers exiting reactor (3) is fed through adsorber (2) at 200° C. in order to desorb propionitrile from the adsorbent present in adsorber (2). The portion of oligomer products containing propionitrile desorbed from adsorber (2) is handled in the same way as product exiting reactor (3) that has not been used to desorb nitriles: it is sent to fractionation towers (5). With this process, the nitrile, which acts as a poison for the olefin oligomerization catalyst, is effectively "parked" in front of the oligomerization reactor (3), and is released again in the product stream at the exit of the same oligomerization reactor (3), without contacting the olefin oligomerization catalyst at any time.

By switching the flow between adsorbers (2) and (4), and simultaneously desorbing nitrile from the adsorber already contaminated with nitriles, a continuous oligomerization process is established in which the adsorption capacity of the adsorbents present in adsorbers (2) and (4) is sufficient to achieve commercial catalyst lives in reactors (3) for oligomerization. Without such switch of operation between adsorbers (2) and (4), more frequent oligomerization reactor shut down is necessary to allow nitrile desorption from the adsorbent Also, with the switch of flow between adsorbers feed contaminant removal is fully integrated in the higher olefins process and overall long adsorbent lifetimes are achieved.

While the invention has been illustrated above with two adsorbers, more than two adsorbers can be used, as required to allow efficient feed contaminant removal and continuous feed conversion to hydrocarbon products.

The experimental data in Table 1 below demonstrates improved adsorption performance using NaY with a process in accordance with the present invention. Breakthrough is the adsorbent life expressed as g feed/g adsorbent presenting a breakpoint at which the effluent of the adsorbent no longer meets the preferred target and the adsorbent needs to be regenerated or replaced. As can be seen in Table 1, NaY adsorbent demonstrates a higher breakthrough level and therefore needs to be replaced less frequently than conventional adsorbents.

TABLE 1 propionitrile removal

| Adsorbent | Pellets size (mm) | Feed | Flow rate (g/h) | WHSV (h⁻¹) | Temperature (° C.) | Pressure (bar) | Breakthrough (gFeed/gAds) | Notes |
|---|---|---|---|---|---|---|---|---|
| NaY CBV 100 zeolyst | 0.3-0.6 | A | 10 | 10 | 40 | 10 | 720 | (1) |
| Selexsorb CDX BASF | 0.3-0.6 | A | 10 | 10 | 40 | 10 | 397 | (1) |
| Selexsorb CD BASF | 0.3-0.6 | A | 10 | 10 | 40 | 10 | 297 | (1) |
| NaY CBV 100 zeolyst | 0.2-0.4 | B | 9.6 | 3.2 | 40 | 10 | 506 | 1st cycle (2), (3) |
| NaY CBV 100 zeolyst | 0.2-0.4 | B | 9.6 | 3.2 | 40 | 10 | 556 | 2nd cycle (4) |

(1) Initial pretreatment was done in nitrogen at 200° C. for 24 hrs. Adsorption experiment carried out at 35 bar
(2) Regeneration between 1st and 2nd cycle was done at 200° C. and 12 bar using 1-decene during 24 hours
(3) Initial pretreatment was done at 200° C. for 24 hours using 1-Decene at 9.6 g/h flow rate
(4) The 2nd cycle was done after regeneration without any further pretreatment Feed composition:
A. 66 wt % 1-pentene/34 wt % pentane/100 wtppm $H_2O$/80 wtppm propionitrile
B. 100 wt % 1-pentene/100 wtppm $H_2O$/80 wtppm propionitrile

The invention claimed is:

1. A continuous process for oligomerizing an olefin feed which is contaminated with nitriles into a hydrocarbon product comprising oligomers of the olefin feed, the process comprising the steps of:
   (i) in a first adsorber, contacting an olefin feed comprising nitriles with at least one adsorbent in order to remove nitriles from the olefin feed to produce a clean olefin feed with a reduced level of nitriles;
   (ii) oligomerizing the clean olefin feed to produce the hydrocarbon product which comprises the oligomers of the olefin feed;
   (iii) before the at least one adsorbent in the first adsorber is saturated with nitriles, switching the flow of the olefin feed comprising nitriles from the first adsorber to a second adsorber;
   (iv) in a second adsorber, contacting the olefin feed comprising nitriles with at least one adsorbent in the second adsorber in order to remove nitriles from the olefin feed to produce additional clean olefin feed;
   (v) while step (iv) is taking place, desorbing the at least one adsorbent having nitriles of the first adsorber before it is saturated with nitriles with a portion of the hydrocarbon product comprising oligomers of the olefin feed obtained in step (ii) to desorb the nitriles to produce a hydrocarbon product which comprises desorbed nitriles; and
   (vi) sending the hydrocarbon product of step (ii) and the hydrocarbon product which comprises desorbed nitriles of step (v) to fractionation.

2. The process according to claim 1, wherein the clean olefin feed is contacted in oligomerizing step (ii) with a catalyst under conditions that are suitable to oligomerize the clean olefin feed.

3. The process according to claim 2, wherein the olefin in the clean olefin feed is selected from olefins having 3 to 6 carbon atoms.

4. The process according to claim 2, wherein the catalyst used in oligomerizing step (ii) is a zeolite, nickel oxide, phosphoric acid, or combinations thereof.

5. The process according to claim 1, wherein the at least one adsorbent comprises a zeolite with the faujasite structure.

6. The process according to claim 5, wherein the zeolite comprises sodium zeolite Y (NaY).

7. The process according to claim 6, wherein the zeolite comprises sodium zeolite X (NaX).

8. The process according to claim 1, wherein the switching is automated.

9. The process according to claim 1, wherein the first adsorber and the second adsorber are equipped with tube heating.

10. The process according to claim 1, wherein the first and second adsorbers are heated by heat generated during step (ii).

11. The process according to claim 1, wherein nitrile adsorption in step (i) is carried out at a temperature of 20° C. to 60° C. and nitrile desorption in step (v) is carried out at a temperature of 150° C. to 250° C.

12. The process according to claim 1, wherein the nitriles are selected from acetonitrile, propionitrile and mixtures thereof.

13. The process according to claim 1, wherein the olefin feed and the hydrocarbon product comprising oligomers of the olefin feed flow counter-currently.

14. The process according to claim 1, wherein the desorbong step (v) is carried out with a derivative of the portion of the hydrocarbon product comprising oligomers of the olefin feed.

* * * * *